US012458761B2

(12) United States Patent
Shaw et al.

(10) Patent No.: US 12,458,761 B2
(45) Date of Patent: Nov. 4, 2025

(54) DOSAGE VERIFICATION SYSTEM AND METHOD FOR SAFETY SYRINGE

(71) Applicants: Retractable Technologies, Inc., Little Elm, TX (US); Thomas J. Shaw, Frisco, TX (US)

(72) Inventors: Thomas J. Shaw, Frisco, TX (US); Kathryn Duesman, Pilot Point, TX (US); Mark Small, Heavener, OK (US); Ni Zhu, McKinney, TX (US)

(73) Assignee: Retractable Technologies, Inc., Little Elm, TX (US)

( * ) Notice: Subject to any disclaimer, the term of this patent is extended or adjusted under 35 U.S.C. 154(b) by 0 days.

(21) Appl. No.: 17/929,169

(22) Filed: Sep. 1, 2022

(65) Prior Publication Data

US 2024/0075216 A1 Mar. 7, 2024

(51) Int. Cl.
*A61M 5/315* (2006.01)
*A61M 5/31* (2006.01)
(Continued)

(52) U.S. Cl.
CPC .... *A61M 5/31578* (2013.01); *A61M 5/31535* (2013.01); *A61M 5/31545* (2013.01);
(Continued)

(58) Field of Classification Search
CPC .......... A61M 5/31578; A61M 5/31535; A61M 5/31545; A61M 2005/3126; A61M 2205/18; A61M 2205/3569; A61M 2205/3592; A61M 2005/3125; A61M 5/178; A61M 5/31; A61M 5/315; A61M 5/31565; A61M 5/31533; A61M 5/31566;
(Continued)

(56) References Cited

U.S. PATENT DOCUMENTS

| | | | |
|---|---|---|---|
| 2,117,469 | A | 5/1938 | Woodyatt |
| 2,860,635 | A | 11/1958 | Wilburn |

(Continued)

FOREIGN PATENT DOCUMENTS

| | | | |
|---|---|---|---|
| CN | 102068734 | A | 5/2011 |
| CN | 102573959 | A | 7/2012 |

(Continued)

*Primary Examiner* — Jason E Flick
(74) *Attorney, Agent, or Firm* — Scheef & Stone, LLP; Robin L. Barnes; Mike Schofield

(57) ABSTRACT

A dosage verification system for use prior to administering an injection of a medicinal fluid drawn into a medical syringe, the system comprising a medical syringe having a barrel with an outwardly facing, flat indicia display surface, plunger having a plunger seal disposed inside and slidably engaging an inwardly facing wall of the barrel and a plunger handle projecting rearwardly from the barrel, and a hypodermic needle projecting forwardly from the barrel, all in combination with an imaging device configured to view and selectively capture, store or transmit a digital image of the plunger position relative to the barrel when a dose of the medicinal fluid is drawn into the fluid chamber of the barrel prior to an injection to verify and provide a record of the dosage drawn, and to alert a user prior to injection when an incorrect dosage is drawn into the fluid chamber of the syringe.

41 Claims, 8 Drawing Sheets

(51) Int. Cl.
*A61M 5/32* (2006.01)
*G08B 21/18* (2006.01)
*G16H 20/17* (2018.01)

(52) U.S. Cl.
CPC ........... *G08B 21/182* (2013.01); *G16H 20/17* (2018.01); *A61M 2005/3126* (2013.01); *A61M 2205/18* (2013.01); *A61M 2205/3569* (2013.01); *A61M 2205/3592* (2013.01)

(58) Field of Classification Search
CPC .......... A61M 5/31548; A61M 5/31561; A61M 2205/35; A61M 2205/3576; G08B 21/182; G16H 20/17; G16H 20/10; G16H 20/00
See application file for complete search history.

(56) References Cited

U.S. PATENT DOCUMENTS

| | | | | |
|---|---|---|---|---|
| 4,573,976 | A | 3/1986 | Sampson et al. | |
| 4,650,468 | A | 3/1987 | Jennings, Jr. | |
| 4,702,738 | A | 10/1987 | Spencer | |
| 4,790,828 | A | 12/1988 | Dombrowski et al. | |
| 4,840,619 | A | 6/1989 | Hughes | |
| D302,726 | S | 8/1989 | Schwobel | |
| 4,915,696 | A | 4/1990 | Felmer | |
| 4,946,447 | A | 8/1990 | Hardcastle et al. | |
| 4,994,034 | A | 2/1991 | Botich et al. | |
| 5,037,402 | A | 8/1991 | Bartman | |
| 5,049,133 | A | 9/1991 | Villen Pascual | |
| 5,053,010 | A | 10/1991 | McGary | |
| 5,084,018 | A | 1/1992 | Tsao | |
| 5,092,461 | A | 3/1992 | Adam | |
| 5,215,534 | A | 6/1993 | DeHarde et al. | |
| 5,312,372 | A | 5/1994 | DeHarde et al. | |
| 5,407,436 | A | 4/1995 | Toft | |
| 5,437,647 | A | 8/1995 | Firth et al. | |
| 5,445,616 | A | 8/1995 | Adobbati | |
| 5,445,618 | A | 8/1995 | Adobbati | |
| 5,456,668 | A | 10/1995 | Ogle, II | |
| D377,687 | S | 1/1997 | Udovch | |
| 5,672,161 | A | 9/1997 | Allen et al. | |
| 5,782,804 | A | 7/1998 | McMahon | |
| D420,129 | S | 2/2000 | McMahon | |
| 6,090,077 | A | 7/2000 | Shaw | |
| 6,213,987 | B1 | 4/2001 | Hirsch et al. | |
| 6,290,678 | B1 | 9/2001 | Aydelotte | |
| 6,416,323 | B1 | 7/2002 | Grenfell et al. | |
| 6,514,261 | B1 | 2/2003 | Randall et al. | |
| 6,585,690 | B1 | 7/2003 | Hoeck et al. | |
| 7,115,113 | B2 | 10/2006 | Evans | |
| D601,242 | S | 9/2009 | Bierman et al. | |
| D601,243 | S | 9/2009 | Bierman et al. | |
| D673,670 | S | 1/2013 | Linnenschmidt | |
| 8,372,044 | B2 | 2/2013 | Westbye et al. | |
| 8,512,279 | B2 | 8/2013 | Klein | |
| 8,540,670 | B2 | 9/2013 | Wayman | |
| D693,003 | S | 11/2013 | Wang | |
| 9,044,552 | B2 | 6/2015 | Schraga | |
| 9,138,545 | B2 | 9/2015 | Shaw | |
| 9,173,726 | B2 | 11/2015 | Sabourin | |
| 9,308,353 | B1 | 4/2016 | Shaw et al. | |
| 9,320,469 | B2 | 4/2016 | Shaw et al. | |
| 9,381,309 | B2 | 7/2016 | Shaw | |
| 9,623,192 | B2 | 4/2017 | Chin et al. | |
| D792,969 | S | 7/2017 | Taylor | |
| D793,549 | S | 8/2017 | Defusco | |
| D793,550 | S | 8/2017 | Defusco | |
| 9,814,841 | B2 | 11/2017 | Shaw | |
| D805,199 | S | 12/2017 | Chen et al. | |
| D812,748 | S | 3/2018 | Funakoshi et al. | |
| D814,630 | S | 4/2018 | Finke et al. | |
| D815,732 | S | 4/2018 | Mills et al. | |
| 9,931,475 | B2 | 4/2018 | Shaw | |
| 9,956,352 | B2 | 5/2018 | Shaw et al. | |
| D823,457 | S | 7/2018 | Shaw et al. | |
| D823,461 | S | 7/2018 | Shaw et al. | |
| D823,463 | S | 7/2018 | Shaw et al. | |
| D829,891 | S | 10/2018 | Shaw et al. | |
| D832,423 | S | 10/2018 | Ishida | |
| 10,086,141 | B2 | 10/2018 | Steel et al. | |
| D835,265 | S | 12/2018 | Inoue | |
| D836,772 | S | 12/2018 | Nandi | |
| D838,842 | S | 1/2019 | Shaw et al. | |
| D851,757 | S | 6/2019 | Nandi | |
| 10,525,207 | B2 | 1/2020 | Zivkovic et al. | |
| 10,568,554 | B2 | 2/2020 | Shaw et al. | |
| 10,625,028 | B2 | 4/2020 | Shaw et al. | |
| D894,381 | S | 8/2020 | Shaw et al. | |
| D914,871 | S | 3/2021 | Shaw | |
| D914,872 | S | 3/2021 | Shaw et al. | |
| D914,873 | S | 3/2021 | Shaw | |
| D914,874 | S | 3/2021 | Shaw | |
| D914,875 | S | 3/2021 | Shaw | |
| 11,000,217 | B2 | 5/2021 | Shaw et al. | |
| 11,141,570 | B2 | 10/2021 | Shaw et al. | |
| 11,246,989 | B1 | 2/2022 | Halbach | |
| 2002/0065488 | A1 | 5/2002 | Suzuki et al. | |
| 2002/0068907 | A1 | 6/2002 | Dysarz | |
| 2002/0082560 | A1 | 6/2002 | Yang | |
| 2003/0028171 | A1 | 2/2003 | DeHarde | |
| 2003/0038171 | A1 | 2/2003 | Lim et al. | |
| 2003/0229316 | A1 | 12/2003 | Hwang | |
| 2004/0024368 | A1 | 2/2004 | Broselow | |
| 2005/0020988 | A1 | 1/2005 | Woehr | |
| 2005/0159706 | A1 | 7/2005 | Wilkinson et al. | |
| 2006/0084925 | A1 | 4/2006 | Ramsahoye | |
| 2006/0178578 | A1 | 8/2006 | Tribble | |
| 2006/0264825 | A1 | 11/2006 | Westbye et al. | |
| 2007/0276338 | A1 | 11/2007 | Shue et al. | |
| 2008/0114306 | A1 | 5/2008 | Bare | |
| 2012/0004621 | A1 | 1/2012 | Shaw et al. | |
| 2012/0022464 | A1 | 1/2012 | Zivkovic et al. | |
| 2013/0023826 | A1 | 1/2013 | Ishida | |
| 2013/0204225 | A1 | 8/2013 | Creaturo | |
| 2014/0012206 | A1 | 1/2014 | Shaw et al. | |
| 2015/0073303 | A1 | 3/2015 | Shaw et al. | |
| 2015/0196714 | A1 | 7/2015 | Creaturo | |
| 2015/0202373 | A1 | 7/2015 | Creaturo | |
| 2015/0231335 | A1 | 8/2015 | Creaturo | |
| 2015/0231355 | A1 | 8/2015 | Creaturo | |
| 2016/0175537 | A1 | 6/2016 | Thorne, Jr. et al. | |
| 2017/0056603 | A1 | 3/2017 | Cowan et al. | |
| 2017/0312439 | A1 | 11/2017 | Kelley | |
| 2018/0154088 | A1 | 6/2018 | Broselow | |
| 2019/0282147 | A1 | 9/2019 | Shaw | |
| 2019/0298928 | A1 | 10/2019 | Shaw et al. | |
| 2019/0298929 | A1* | 10/2019 | Shaw | A61M 5/3129 |
| 2020/0206424 | A1 | 7/2020 | Rios et al. | |
| 2020/0324049 | A1 | 10/2020 | Wilmot | |
| 2020/0381106 | A1 | 12/2020 | Limaye et al. | |
| 2020/0397660 | A1 | 12/2020 | Hernandez et al. | |
| 2022/0054764 | A1 | 2/2022 | Shaw et al. | |
| 2023/0034986 | A1 | 2/2023 | Shaw et al. | |
| 2023/0052321 | A1 | 2/2023 | Shaw | |
| 2023/0080728 | A1 | 3/2023 | Caputo | |
| 2023/0166047 | A1* | 6/2023 | Yarger | A61M 5/3202 604/506 |
| 2024/0075216 | A1 | 3/2024 | Shaw et al. | |
| 2024/0165337 | A1 | 5/2024 | Shaw et al. | |
| 2024/0165341 | A1 | 5/2024 | Shaw | |
| 2024/0226457 | A1 | 7/2024 | Shaw et al. | |
| 2024/0325649 | A1 | 10/2024 | Shaw et al. | |

FOREIGN PATENT DOCUMENTS

| | | | |
|---|---|---|---|
| CN | 104368068 | A | 2/2015 |
| CN | 108619594 | A | 9/2018 |
| DE | 4323466 | | 7/1993 |
| FR | 2809627 | | 12/2001 |
| JP | 2010098323 | | 2/2010 |
| JP | 2016529078 | | 9/2016 |
| WO | 2010098323 | | 2/2010 |

(56) References Cited

FOREIGN PATENT DOCUMENTS

| | | | |
|---|---|---|---|
| WO | 2013050475 | | 4/2013 |
| WO | 2014150201 | | 9/2014 |
| WO | 2016055620 | A1 | 4/2016 |
| WO | WO2016176523 | | 11/2016 |

* cited by examiner

DOSAGE VERIFICATION SYSTEM AND METHOD FOR SAFETY SYRINGE

TECHNICAL FIELD

This invention relates to a system useful for quickly and reliably providing visual verification of medicinal doses drawn into a medical syringe prior to injecting a medication or vaccine into a patient or into another liquid infusion device. The subject system can be used to verify a dosage prior to an injection and to create a reliable visual record of the dosage administered if a question arises after an injection as to whether the dosage administered was correctly drawn or possibly constituted a medical error. One aspect of the subject system relates to a portable imaging device used in combination with a specially configured medical syringe to capture and record a digital image showing the volumetric scale, and preferably the whole volumetric scale, of a medical syringe and the position of the plunger and plunger seal inside the barrel of the syringe after drawing a dose of medicinal fluid. Another aspect of the invention relates to a medical syringe comprising a transparent or translucent barrel having at least one flat side forming an indicia display surface and a volumetric scale with numeric indicia disposed on the indicia display surface and overlying a fluid chamber extending longitudinally through the barrel to facilitate capturing and recording a digital image of the volume of a medicinal fluid drawn into the fluid chamber by a plunger slidably engaging an inwardly facing wall defining the circumferentially extending sidewall of the fluid chamber. Another aspect of the invention relates to a medical syringe comprising a barrel with a fluid chamber of known maximum useful volume in combination with a portable imaging system configured to capture a digital image of the syringe and determine the drawn dosage of a medicinal fluid from the position of the plunger handle relative to the barrel using ratio and proportion.

Still another aspect of the invention relates to a system comprising a medical safety syringe with a flat indicia display surface and a volumetric scale overlying a fluid chamber in combination with a digital imaging device configured to capture, record and optionally transmit a digital image of a medicinal fluid drawn into the fluid chamber to verify the dosage before administering the medicinal fluid to a patient. Still another aspect of the subject invention relates to the combination of a mobile digital imaging device such as a cellular telephone or digital tablet that is configured by application software resident in the device to enable a user of the device to capture, index and store digital images of a medical syringe containing a drawn dose of a fluid medication, generate a digital or documentary report, and trigger a visual, audio or tactile alert and/or alarm if the drawn dosage does not conform to a predetermined acceptable standard.

Still another aspect of the invention relates to a method for verifying the dose of a medicinal fluid drawn into a medical syringe prior to injecting the medicinal fluid into a patient or liquid infusion apparatus. As used in this disclosure, "medical syringe" refers to a medical device having an elongate barrel, generally made of a medical grade injection molded plastic, such as polypropylene, having a plunger with an elastomeric plunger seal slidably engaging an inwardly facing, cylindrical wall of the barrel that cooperate to define a fluid chamber disposed in fluid communication with a forwardly projecting hypodermic needle that is typically covered by a protective needle cap prior to use. As used in this disclosure, the term "safety syringe" is intended to refer to a medical syringe having the capability of causing the pointed tip of a hypodermic needle to be biased or retracted into a needle retraction cavity or to be covered with a protective guard or safety shield following use for the avoidance of accidental needle stick injuries.

BACKGROUND OF THE INVENTION

Ways to identify and reduce the cause and occurrence of medical errors are a primary concern of the healthcare and insurance industries. A medical error is a preventable adverse effect of medical care, whether or not it is evident or harmful to the patient. Two commonly occurring sources of medical errors are the administration of the wrong drug or the wrong dosage of the right drug to a patient. Various protocols have been instituted in an effort to reduce such medical errors but they remain a principal concern. In many healthcare facilities, a medical caregiver must have another person verify the medicine and the drawn dosage prior to administering an injection to a patient. In situations where an adverse outcome arises during or following patient treatment, a verifiable record is needed to assist investigators in determining whether one causative factor was the dosage administered from a syringe by a healthcare worker. Similarly, in instances where injections are self-administered, such as with insulin injections, a verifiable record can assist in determining whether or not an incorrect dosage may have been a producing cause of an adverse outcome.

One difficulty that has arisen with the use of conventional medical syringes, and particularly with low-dose syringes such as 1 mL or 0.5 mL, is that the radius of curvature of the cylindrical barrels is so small that the volumetric indicia and associated numerals are difficult or impossible to print onto the barrel during manufacture and are also difficult to read when positioned so that they curve or wrap around the barrel. In many cases, and particularly where the medicinal fluid being injected is clear and colorless, a user may not be able to see and accurately determine the fluid dosage drawn into a syringe prior to an injection.

Another principal safety concern of healthcare institutions and medical caregivers are accidental needlestick injuries that can occur prior, during or subsequent to administering an injection. Such injuries are often preventable or controllable by appropriate product design and by strict adherence to safety protocols relating to the storage, use and post-use handling and disposal of needle products contaminated with blood-borne pathogens. A system is needed that can provide an accurate historical record of dosages drawn and administered with medical syringes while also effectively reducing the incidence and likelihood of accidental needle stick injuries.

SUMMARY OF THE INVENTION

One embodiment of the invention disclosed here is a system comprising the combination of a medical syringe having a barrel with a flat, outwardly facing image display surface, a volumetric scale disposed on the flat image display surface overlying an elongate cylindrical fluid chamber inside the barrel, and a portable imaging device desirably configured to capture and store a digital image of at least a portion of the volumetric scale in relation to the dosage of a medicinal fluid drawn into the fluid chamber prior as viewed through a single wall of the barrel prior to administering an injection. In a preferred embodiment of the invention, the portable imaging device is a mobile device such as a cellular telephone or digital tablet equipped with a camera system that can focus on, capture and store a digital image of the entire volumetric scale of the medical syringe in a single frame in which the position of the plunger seal inside the barrel and the dosage level of a medicinal fluid present in the fluid chamber of the syringe barrel is also recorded. In another preferred embodiment of the invention, the digital imaging device is desirably configured and calibrated to record a digital image showing the position of a plunger handle relative to a syringe barrel comprising a fluid chamber of known volume from which the dosage level of a medicinal fluid drawn into the syringe can be calculated or otherwise determined.

In another preferred embodiment of the invention, the medical syringe is used in combination with a portable imaging device and also comprises a needle safety feature to reduce the likelihood of accidental needle sticks to patients, healthcare workers and subsequent handlers following use and during disposal of such syringes. One such needle safety feature comprises, for example, a needle retraction mechanism that biases and repositions the needle tip into a protected position relative to a needle retraction cavity following an injection. Another such needle safety feature comprises, for example, a needle safety shield that is forwardly slidable to cover the forwardly projecting tip of a hypodermic needle following an injection.

In one embodiment of the system of the invention, the imaging device is a cellular phone or digital tablet comprising application software downloadable from a proprietary service provider that is specially configured to scan, capture, record, display, store and index digital images of medical syringes for the purpose of determining and recording the dosage of medicinal fluid drawn into a syringe prior to administering an injection or infusion. Other ancillary components, functions and capabilities of such a system can be resident in the imaging device or provided as auxiliary components of the subject system. Such ancillary or auxiliary components an include a transmitter for forwarding digital images via wired or wireless connections; an optional comparator useful for determining whether doses of medicinal fluids drawn into a syringe are within permissible ranges or deviations from predetermined or preset values; an audio, visual or tactile alert generator signifying incorrect dosages; a digital display; a digital storage device or media; and a report generator useful for indexing and reporting digital data to be viewed, printed, or integrated into other electronic medical records. The dosage verification system can optionally be linked to a database of acceptable dosages for particular medicaments and patient profiles, and the dosage verification scans can, for example, be uploaded into digitized patient records accessible to various classes of identified user groups. Such user groups can include, for example, hospital risk managers, pharmacy managers, insurance managers, and the like.

According to one embodiment of the method of the invention, a dose of a medicinal fluid is drawn into the fluid chamber of a syringe, preferably a safety syringe, that is provided for use in combination with a portable digital imaging device to view through a single wall, capture, store and otherwise process a digital image of the dose drawn into the syringe. The digital image is useful for checking to see that the correct dosage of medicinal fluid has been drawn prior to injection and is also useful for providing an electronic or documentary record that can be used later to verify the dosage previously administered. A preferred syringe for use in practicing the subject method is a safety syringe comprising a barrel with an outwardly facing, flat, indicia display surface forming the outside portion of at least one side of an integrally molded, transparent polymeric wall that is desirably integrally molded together with the inwardly facing wall of an elongate cylindrical fluid chamber extending longitudinally through the barrel. In this embodiment, the method of the invention is practiced by drawing an intended dosage of a fluid medication (or vaccine) into a medical syringe; positioning the syringe so that the individual indicia and associated Arabic numerals of a volumetric scale disposed on a flat, outwardly facing indicia display surface of the syringe barrel are clearly visible in juxtaposition to the medicinal fluid level inside the syringe; positioning a portable imaging device so that a digital camera or scanner has a clear and unobstructed view of the medicinal fluid level inside the fluid chamber and of the volumetric indicia overlying the fluid chamber of the syringe; capturing a digital image of the medicinal fluid level inside the syringe; and saving the digital image in an archivable format that is recordable for use in verifying the dosage administered at a future time. In one variation of the subject embodiment of the method of the invention, the portable imaging device can be configured to compare the drawn dosage of the medicinal fluid to a predetermined value as soon as the image is captured and, if the drawn dosage is incorrect or outside an acceptable margin of error, trigger a visible, audible or tactile alert that will cause the user or medical caregiver to reassess the dosage being administered prior to giving the injection. In another variation of the subject embodiment, the image data can be merged into a template configured to generate a report suitable for inclusion in the appropriate medical records.

According to another embodiment of the method of the invention, a dose of a medicinal fluid is drawn into the fluid chamber of a medical syringe of known volume (e.g., 0.5 mL, 1 mL, 3 mL, etc.) that is provided for use in combination with a portable digital imaging device to view, capture, store and otherwise process a digital image of the plunger position relative to the barrel. In this embodiment of the invention, the portable imaging device is preferably configured by application software or other similarly effective means to determine the volume of the drawn dose of medicinal fluid from the position of the plunger handle relative to the barrel as compared to the plunger position when the plunger is positioned to utilize the full rated volume of the syringe. This method of determining the drawn dosage of a medicinal fluid by ratio and proportion can also be used with syringes not having a transparent barrel wall.

Other benefits and advantages of the subject system will likewise become more apparent to those of ordinary skill in the art upon reading this disclosure in relation to the accompanying drawings.

BRIEF DESCRIPTION OF THE DRAWINGS

The system of the invention is further described and explained in relation to the following drawings wherein.

DESCRIPTION OF PREFERRED EMBODIMENTS

Figure 1:
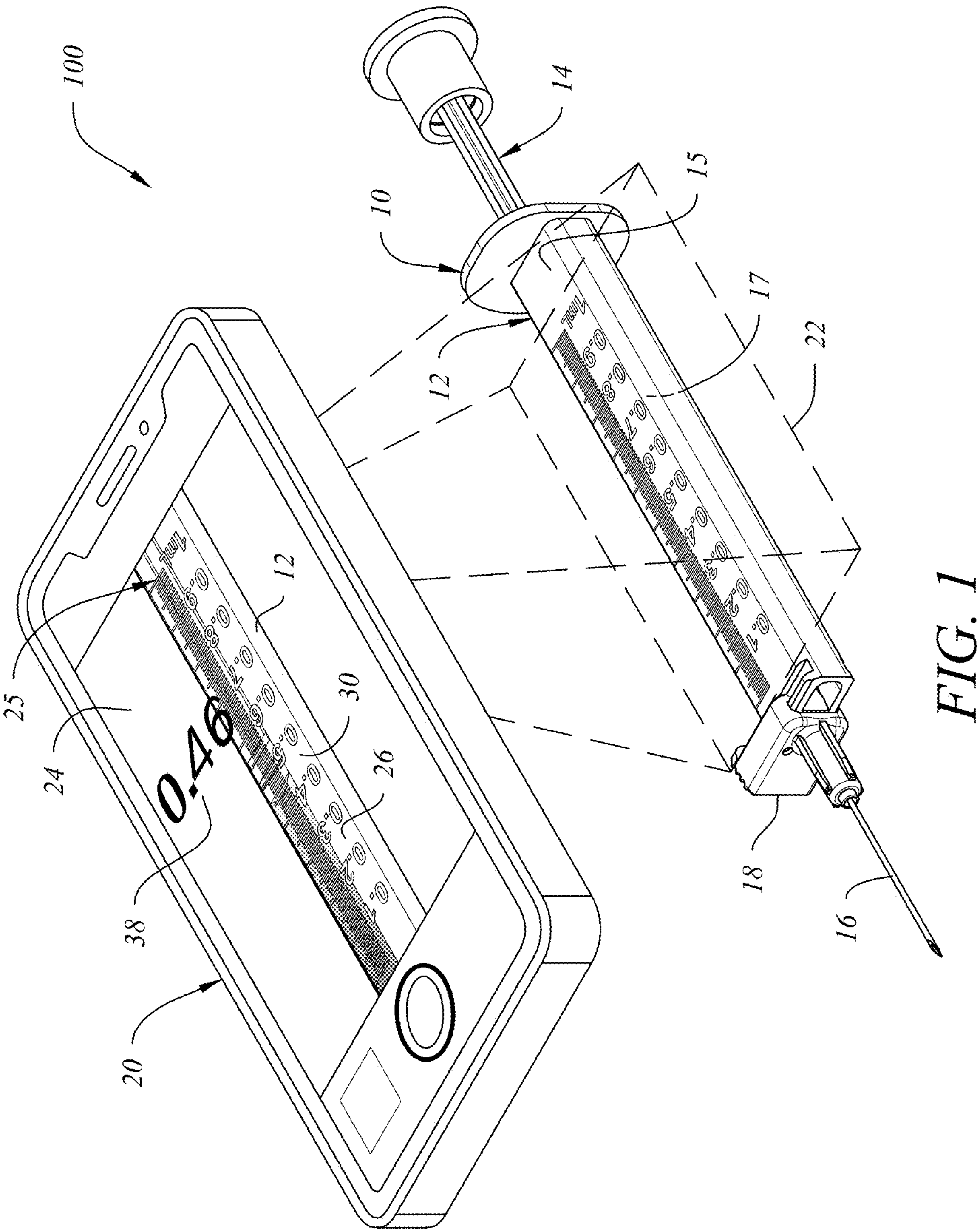
FIG. 1 is a top perspective view of an embodiment of the system showing a cellular telephone having a digital imaging capability disposed in a use position above a medical syringe containing a drawn dose of a medicinal fluid.
Figure 2:
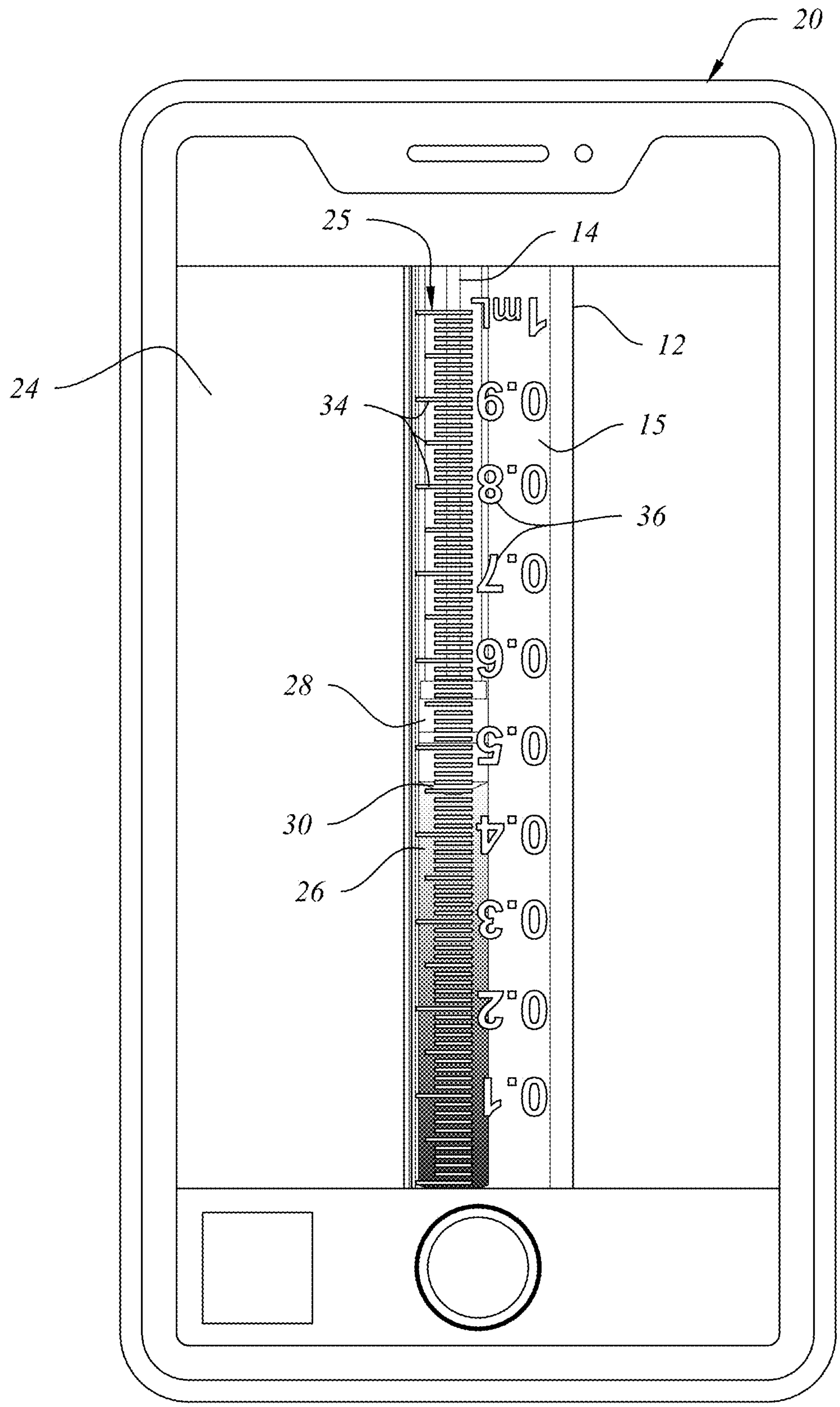
FIG. 2 is an enlarged top plan view of the cellular telephone of the system of FIG. 1 with a digital image showing a volumetric scale and numeric indicia disposed on an upwardly facing surface of syringe barrel overlying a fluid chamber containing a drawn dose of a medicinal fluid (shaded)
Figure 5:
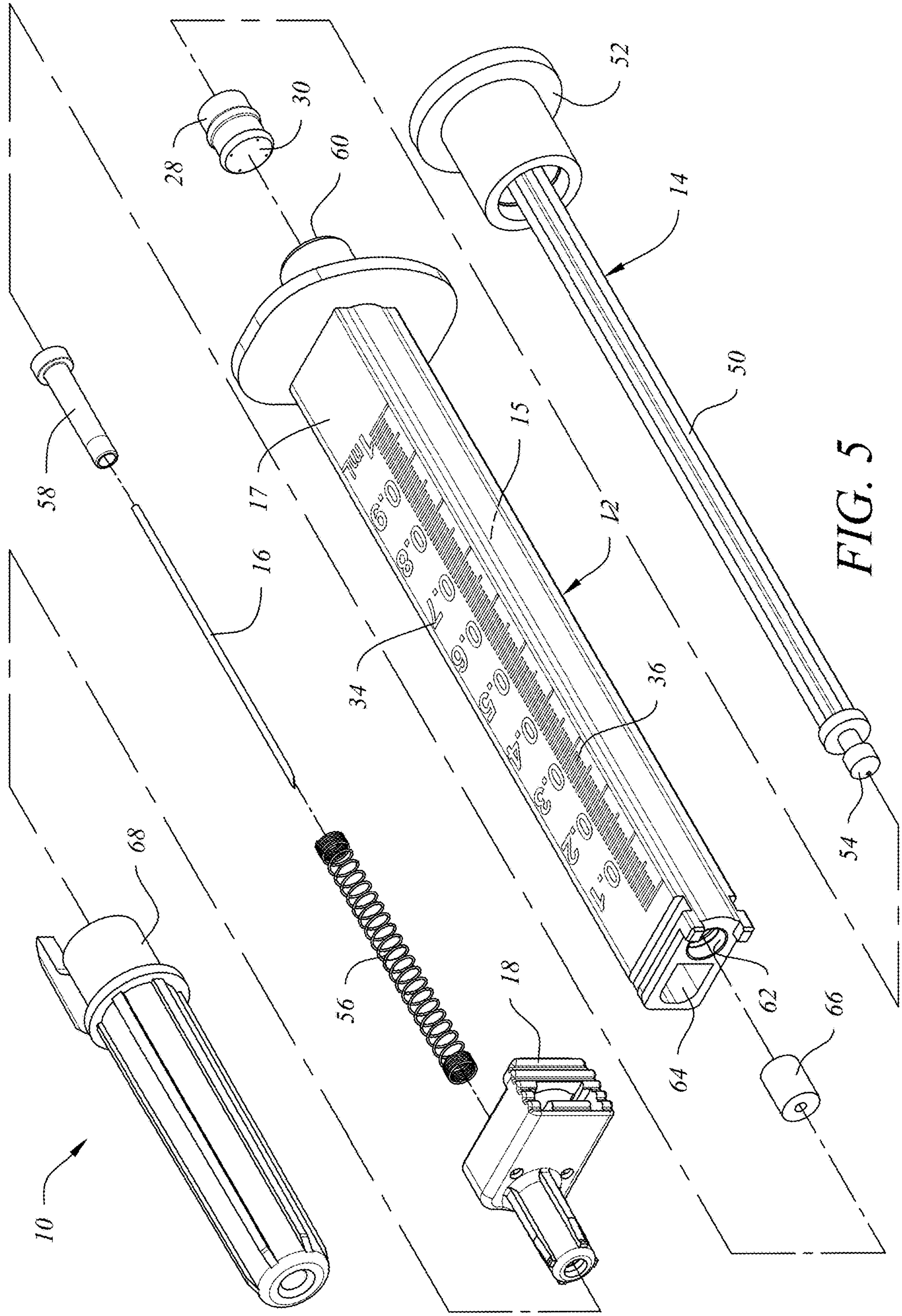
FIG. 5 is an exploded front perspective view of a medical syringe substantially as shown in FIGS. 1 and 3 but rotated 180° around the longitudinal axis so that the downwardly facing flat surface 17 of barrel 12 in FIG. 1 is facing upwardly in FIG. 5.

Referring to FIGS. 1, 2 and 5, one embodiment of dosage verification system 100 comprises a specially designed and configured safety medical syringe 10 in combination with a mobile imaging device 20 configured to capture a digital image display window 24 from a viewing field 22. It will be appreciated that the dimensions of viewing field 22 can vary in accordance with the spacing between safety medical syringe 10 and mobile imaging device 20 and with the lenses, focal lengths and circuitry of mobile imaging device 20. In one preferred embodiment as shown in FIG. 1, viewing field 22 desirably covers the full length of volumetric scale 25 disposed on flat, outwardly facing, indicia display surface 15 of barrel 12 of safety medical syringe 10.

Barrel 12 is desirably unitarily molded from a transparent or translucent medical grade polymer and comprises a volumetric scale 25 having incremental markings 36 and accompanying numerical indicia 34 disposed on flat, outwardly facing indicia display surface 15 (oppositely facing indicia display surface 17 in FIG. 5) to overlie and facilitate simultaneous viewing of a fluid dosage 26 disposed inside longitudinally extending, cylindrical fluid chamber 62 (FIG. 5) that is slidably engaged and bounded rearwardly by the forwardly facing surface 30 of plunger seal 28 mounted on forwardly extending projection 54 of plunger handle 50 of plunger 14. Barrel 12 further comprises a forwardly projecting hypodermic needle 16 that is coaxially aligned with longitudinally extending, cylindrical fluid chamber 62. Hypodermic needle 16 is rearwardly biased inside transversely slidable frontal attachment 18 prior to an injection. As discussed in greater detail below, cylindrical fluid chamber 62 inside barrel 12 has an inwardly facing wall that is desirably unitarily molded with outwardly facing, flat indicia display surfaces 15, 17. Barrel 12 is desirably sufficiently transmissive to light that the forwardly extending end 30 of plunger seal 28 and medicinal fluid 26 drawn into fluid chamber 26 are clearly visible in digital image display window 24 (FIGS. 1 and 2) of mobile imaging device 20.

As depicted in FIGS. 1 and 2, mobile imaging device 20 is a cellular telephone with a camera system and imaging capabilities that are desirably configured by applications software to superimpose a digital readout of the fluid dosage drawn in medical syringe 10 as "0.46" mL. Grayscale shading in FIGS. 1 and 2 is intended to show for illustrative purposes the volume of medicinal fluid 26 drawn into the fluid chamber of medical syringe 10. In the enlargement depicted in FIG. 2, the drawn dosage of medicinal fluid 26 is more visible, with forwardly facing surface 30 of plunger seal 28 and a portion of handle 50 (FIGS. 5 and 6) of plunger 14 inside barrel 12 also being visible within the borders of digital image display window 24.

Figure 3:
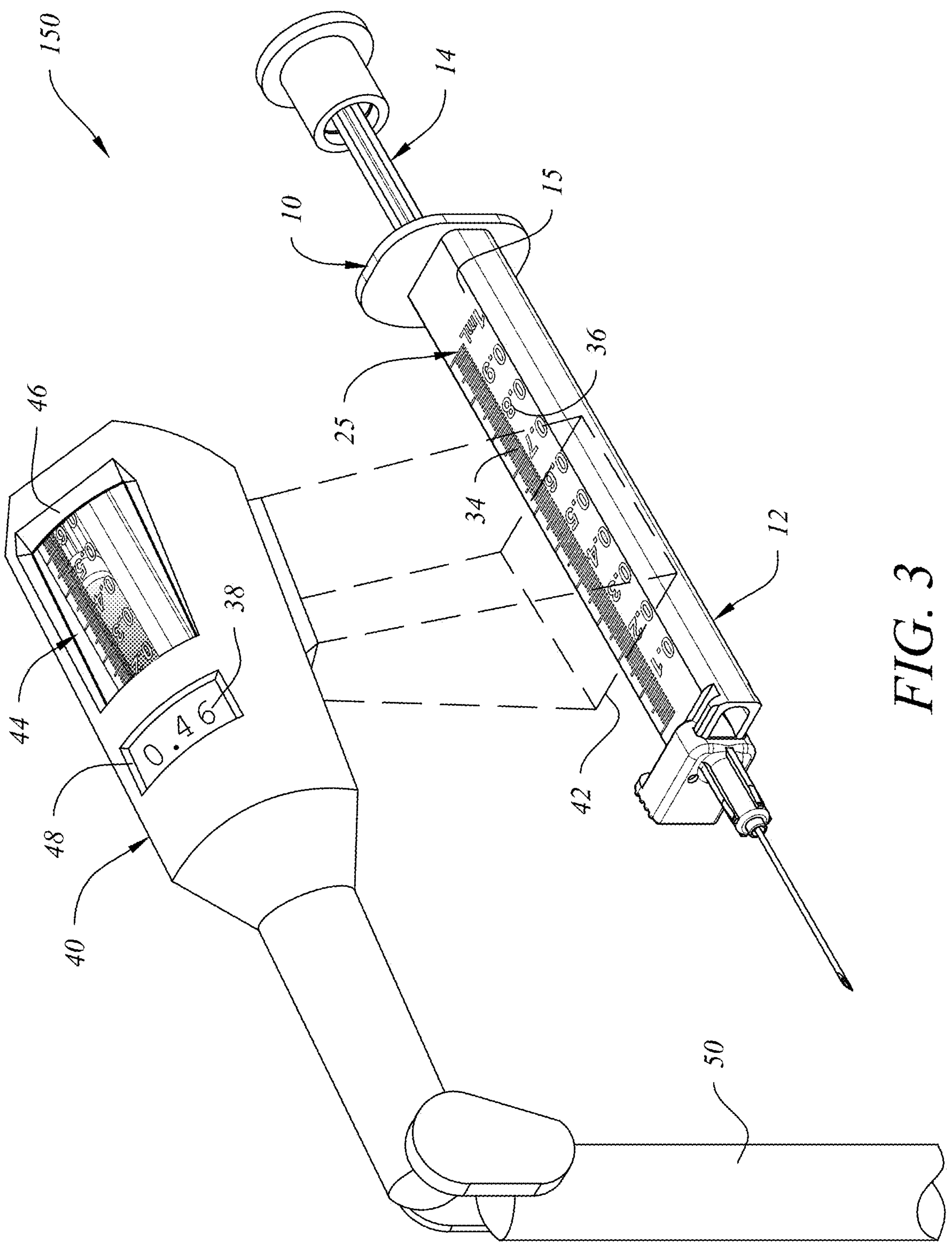
FIG. 3 is a top perspective view of another embodiment of the system showing a portably mounted digital imaging device having a digital imaging capability disposed in a use position above a medical syringe containing a drawn dose of a medicinal fluid.
Figure 4:
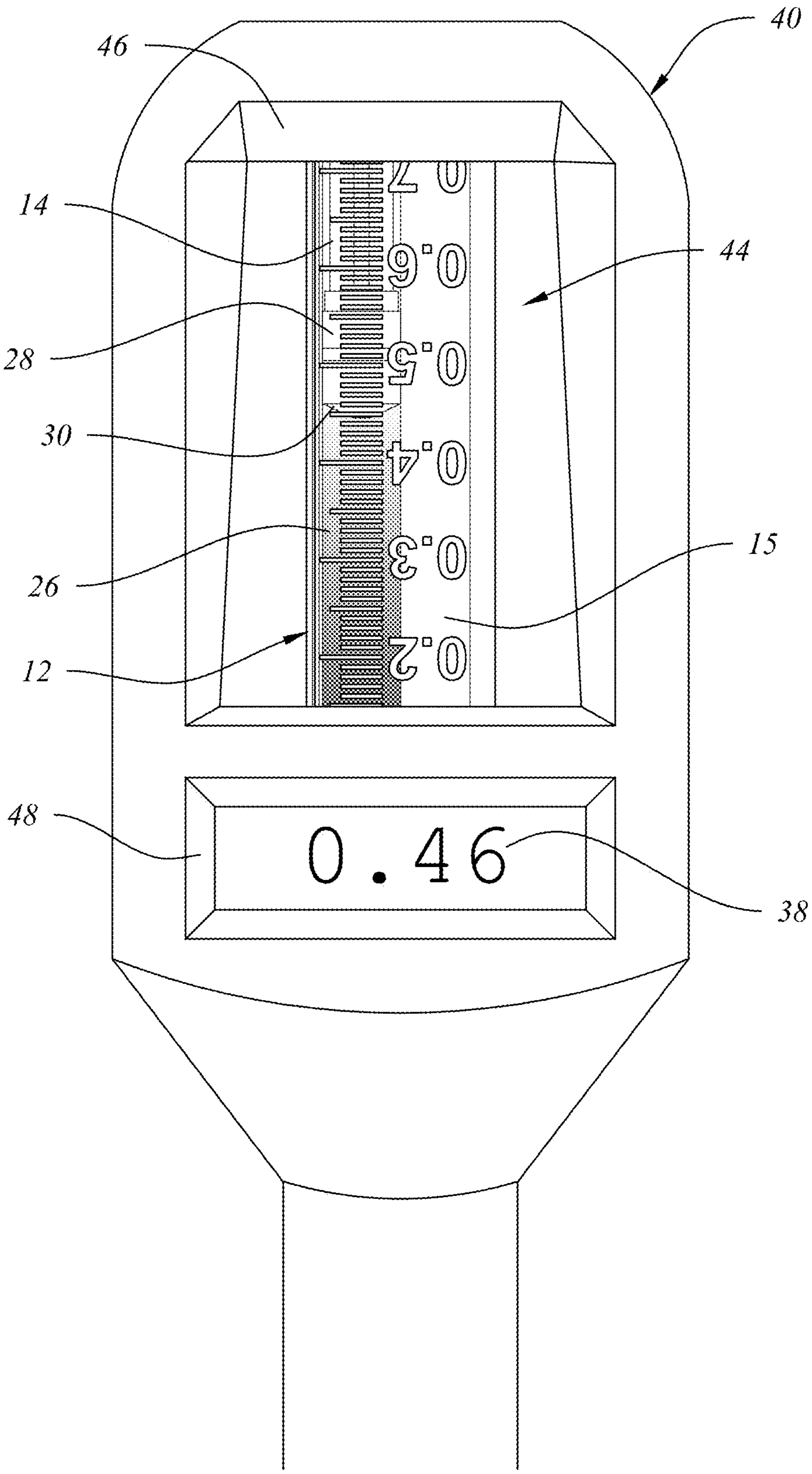
FIG. 4 is an enlarged top plan view of the digital imaging device of FIG. 1 with a digital image showing a volumetric scale and numeric indicia disposed on an upwardly facing surface of syringe barrel overlying a fluid chamber containing a drawn dose of a medicinal fluid (shaded)

Referring to FIGS. 3 and 4, another embodiment of the invention identified as system 150 comprises a digital scanner 40 or other similarly effective, portable digital imaging device that can be mounted to a cart or bed frame in a hospital room or medical treatment area by apparatus such as hinged support rod 50 and adjustably positioned as needed to permit a user or medical caregiver to verify a dose of a medicinal fluid drawn into syringe 10. As previously shown and similarly described in relation to system 100, medical safety syringe 10 desirably comprises a barrel 12 further comprising an outwardly facing flat surface 15 having a volumetric scale 25 with individual indicia 34 and accompanying numerals 36 overlying the elongate fluid chamber inside barrel 12. As shown in FIGS. 3 and 4, digital imaging device 40 comprises a display screen 44 bounded by walls 46 that depicts the image framed within adjustable viewing field 42 focused upon upwardly facing, flat image display surface 15 of barrel 12 of medical syringe 10. Although not shown in FIG. 3, it should be understood that digital imaging device 40 is desirably operatively connected to a laptop or work station configured to capture, process, record, store and transmit digital images as needed to verify the dose of medicinal fluid drawn prior to an injection, trigger an audible, visual or tactile alert as needed if the drawn dosage is incorrect, and produce an archivable record of the dose administered in an injection for possible future use. Referring again to FIGS. 3 and 4, display 44 provides, in a single image, a clear and focused view of a dose of medicinal fluid 26 drawn into the fluid chamber of syringe barrel 12 forwardly of the front surface 30 of plunger seal 28 of plunger 14. Additionally, window 48 of digital imaging device 40 displays a digital readout of "0.46" (mL) as the volumetric dosage of medicinal fluid drawn into barrel 12 of medical syringe 10.

Figure 6:
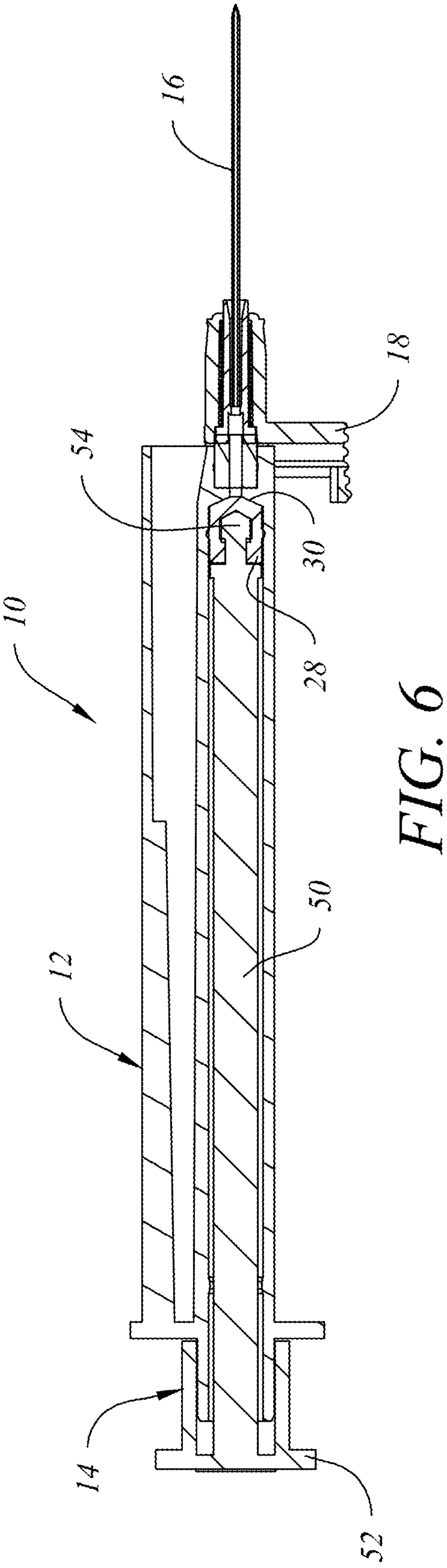
FIG. 6 is a longitudinal cross-sectional view of a medical syringe substantially as shown in FIGS. 1 and 3 with the needle cap removed and the plunger handle fully inserted into the barrel.

The structure and operation of safety medical syringe 10 is further described and explained in relation to FIGS. 5 and 6. Safety medical syringe 10 comprises unitarily molded barrel 12 having two longitudinally extending passageways including fluid chamber 62 defined by a cylindrical, inwardly facing wall and needle retraction chamber 64 and at least one outwardly facing, flat indicia display surface 17 having disposed on it a volumetric scale commensurate with the internal volume of fluid chamber 62. In the embodiment of FIG. 5, for example, there are two oppositely facing, flat indicia display surfaces 15, 17 the volumetric scale extends from 0. 01 to 1.0 mL and comprises both individual markings 36 corresponding to 0.01 mL each and accompanying Arabic reference numerals 34 ranging from 0.1 to 1 mL. Plunger 14 comprising plunger handle 50, distal plunger tip 54 and proximal end cap 52 and an elastomeric plunger seal 28 attachable to distal plunger tip 54 is insertable into rear opening 60 of fluid chamber 62. Annular elastomeric fluid seal 66 is desirably seated inside the front opening of fluid chamber 62 prior to assembling frontal attachment 18 into transverse sliding engagement with the front of syringe barrel 12. Also seated in the forwardly projecting nose of frontal attachment 18 is a needle retraction assembly comprising a forwardly projecting hypodermic needle 16 disposed in fixed relation to elongate needle holder 38 and a compressed retraction spring 56 (shown in its uncompressed state in FIG. 5) that biases needle holder 58 and hypodermic needle 16 rearwardly prior to and during use of medical syringe 10. Needle cap 68 is a protective cap removed by a user prior to drawing a dose into fluid chamber 62 of syringe barrel 12 and should not be used to recap needle 16 following use to avoid needle stick injury to the user.

Referring to FIGS. 5 and 6, medical syringe 10 is depicted in its fully assembled form with plunger handle 50 and plunger seal 28 fully inserted into barrel 12. Needle cap 68 (FIG. 5) is removed to place medical syringe 10 in condition for drawing a dose of a medicinal fluid from a vial (not shown) into the fluid chamber 62 (FIG. 5). Medicinal fluid can enter fluid chamber 62 in front of front surface 30 of plunger seal 28 as plunger cap 52 of plunger 14 is pulled rearwardly after hypodermic needle 16 has been inserted into a vial of medicinal fluid or vaccine. As shown in the embodiment of FIGS. 5 and 6, the safety feature of safety syringe 10 is activated by applying transverse digital pressure to a touchpad of frontal attachment 18, thereby moving hypodermic needle 16 laterally from being coaxially aligned with fluid chamber 62 of barrel 12 to being coaxially aligned with an opening into needle retraction cavity 64 (FIG. 5). This lateral repositioning allows spring 56 to expand, driving needle holder 58 rearwardly into needle retraction cavity and also propelling the front tip end of hypodermic needle 16 rearwardly to a position where the needle tip is no longer exposed and cannot cause an accidental needle stick.

Figure 7:
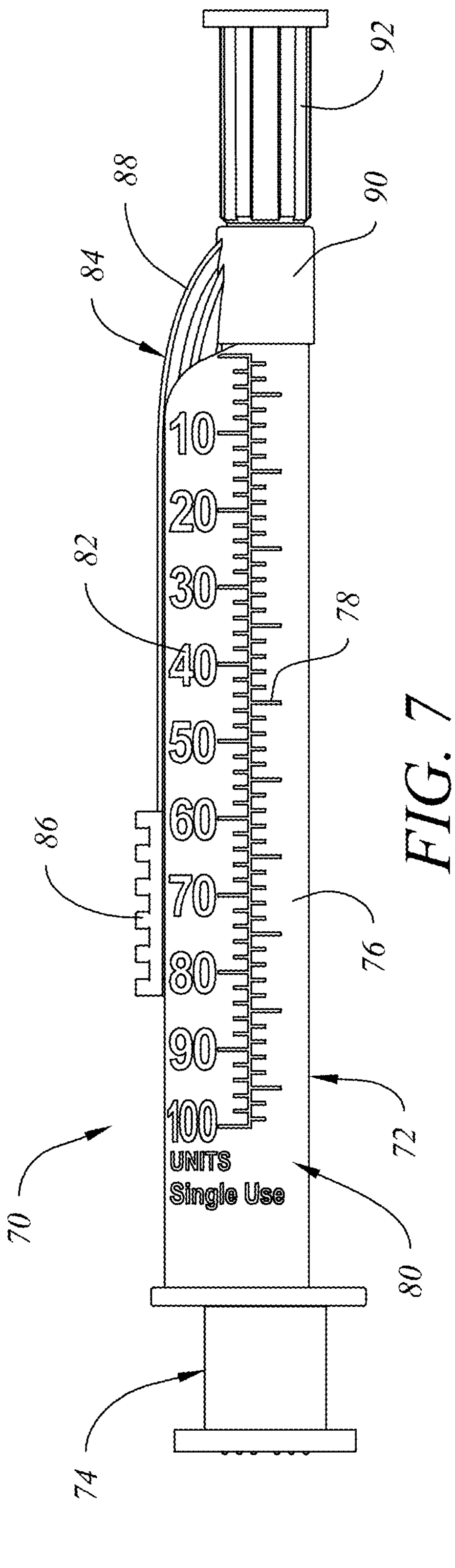
FIG. 7 is a top plan view of another safety medical syringe suitable for use in the system of the invention, with the needle cover in place, the plunger fully inserted into the barrel, and the forwardly slidable needle safety shield disposed in its fully retracted position.
Figure 8:
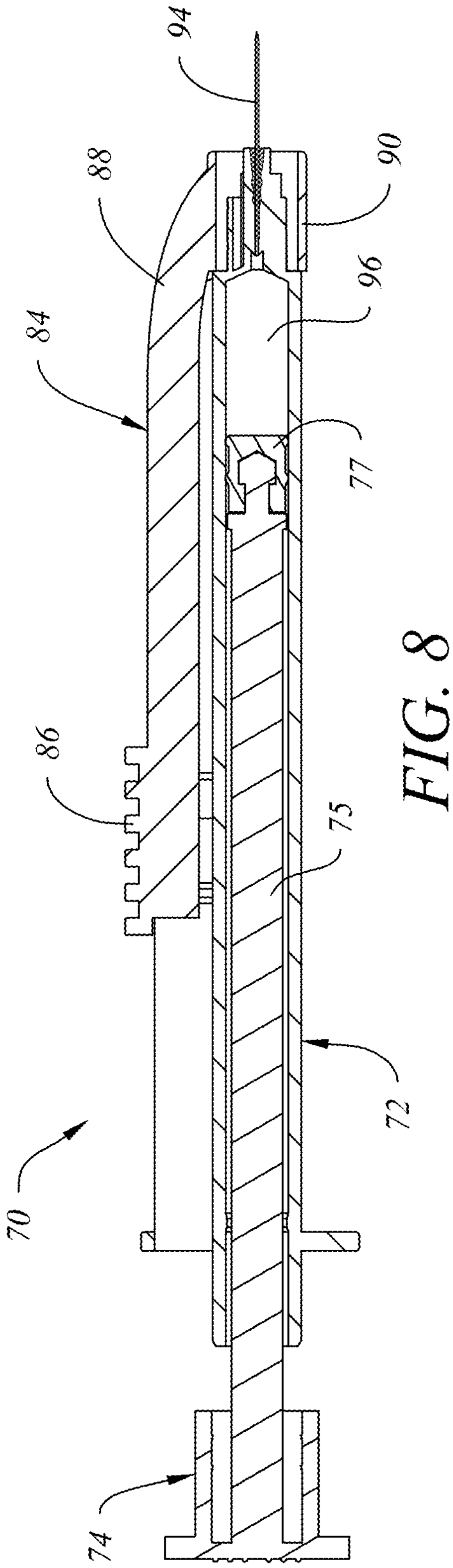
FIG. 8 is a longitudinal cross-sectional view of the medical syringe of FIG. 7 with the needle cover removed to expose the forwardly extending needle tip, the plunger handle partially withdrawn to form a fluid chamber forwardly of the plunger seal, and the forwardly slidable needle safety shield still disposed in its fully retracted position as it would be during an injection.
Figure 9:
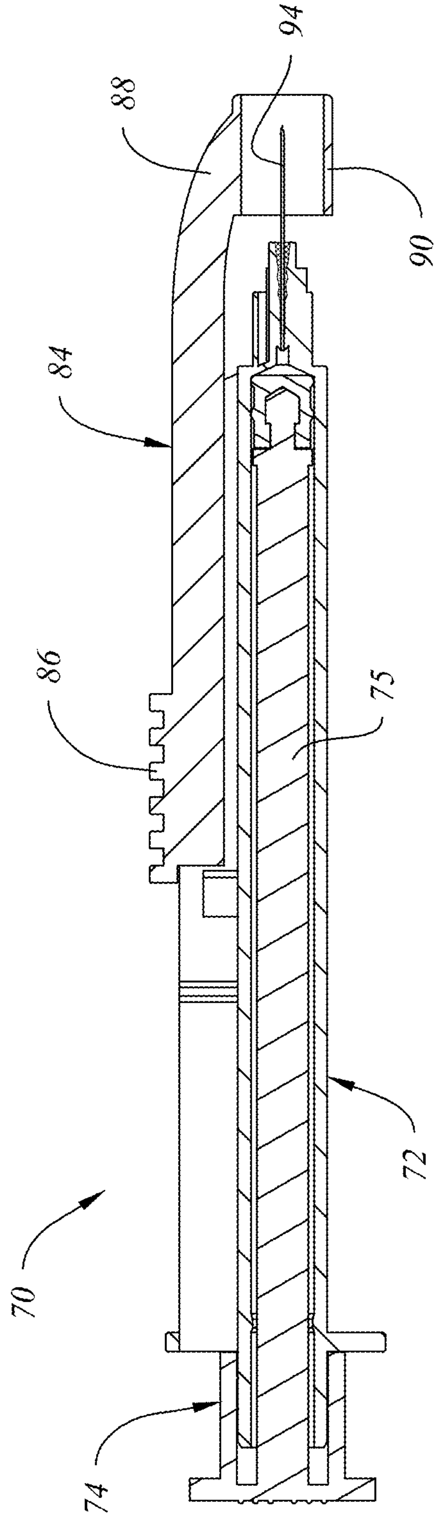
FIG. 9 is another longitudinal cross-sectional view of the medical syringe of FIG. 8 with the plunger fully inserted into the barrel and the forwardly slidable needle safety shield moved to its forwardly extending position with the needle protection guard disposed around the forwardly extending tip of the needle as it would be following an injection.

Another medical safety syringe 70 useful in practicing the system and method of the invention but having a different type of needle safety device is shown in FIGS. 7-9. FIG. 7 shows medical safety syringe 70 prior to use, with needle cap 92 in place. Barrel 72 further comprises an integrally molded, outwardly facing, flat indicia display surface 76 through which fluid chamber 96 (FIG. 8) is visible forwardly of plunger seal 77 when handle 75 of plunger 74 is partially withdrawn relative to barrel 72 when a dose of medicinal fluid is drawn into fluid chamber 96 of barrel 72 of syringe 70. Referring again to FIG. 7, a volumetric dosage scale 80 comprising incremental indicia 78 and accompanying numerical indicia 82 for a single use, 100-unit syringe is disposed on flat indicia display surface 76. Referring to FIGS. 7-8, a slidably engaged needle safety shield 84 having a touch surface 86, actuator handle 88 and circumferentially extending needle guard 90 are depicted in the fully retracted position that leaves the forwardly extending tip of hypodermic needle 94 uncovered and exposed when needle cap 92 is removed prior to use of syringe 70. Referring to FIG. 9, plunger handle 75 of plunger 74 is depicted in the fully inserted position relative to barrel 72 and needle safety shield 84 has been moved forwardly by applying forward pressure to touch surface 86 so that actuator handle 88 causes circumferentially extending needle guard 90 to encircle and protect the forwardly extending tip of hypodermic needle 94 for the avoidance of accidental needle stick injuries.

Figure 10:
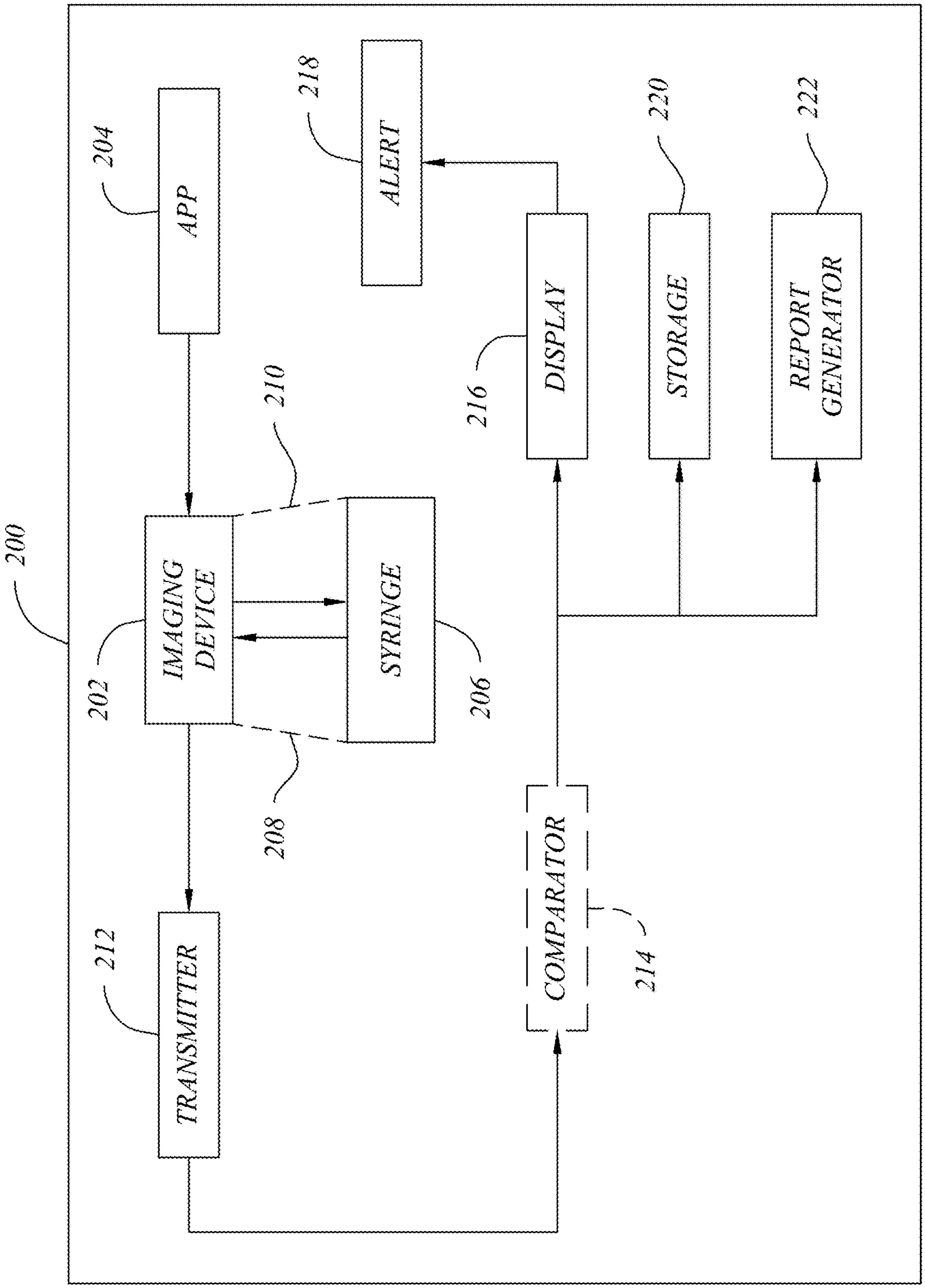
FIG. 10 is a diagrammatic representation of one embodiment of the system of the invention with an imaging device disposed in a use position above a medical syringe and also showing ancillary elements of the system to illustrate its desired functionality.

A simplified diagrammatic view illustrated in FIG. 10 is useful for further describing and practicing an embodiment of the invention identified as dosage verification system 200. Referring to FIG. 10, dosage verification system 200 includes a portable imaging device 202 positioned to view and capture a digital image of the upwardly facing surface of syringe 206 within a viewing field defined by boundaries 208, 210 that is sufficiently large to encompass the full range of a volumetric scale disposed on an upwardly facing, flat indicia display surface of syringe 206 as described previously. In one embodiment of the invention, portable imaging device 202 is configured by application software 204 to focus on and capture a clear image of the indicia display surface and volumetric scale (both individual indicia and accompanying numerals) of the syringe barrel in juxtaposition to the dose of a medicinal fluid drawn into the fluid chamber of the syringe barrel as previously described in relation to FIGS. 1-9 above. Application software 204 can be downloadable onto a mobile imaging device such as a cellular telephone having digital imaging capabilities or accessible by Wi-Fi, internet or other known technologies, and is desirably configured by use of a transmitter 212 or other conventional circuitry to control, process and communicate the digital images and digital image(s) viewed and captured by imaging device 202 to a display 216 and storage device or media 220 (that can be external or embodied in imaging device 202), or operatively linked to a report generator 222 or other archivable and indexed database. According to one embodiment of dosage verification system 200 of the invention, the digital images viewed and captured by imaging device 202 are optionally analyzed in relation to predetermined parameters by a comparator 214 or other similarly effective device or circuitry (with or without transmission to external devices) configured to generate a visual, audible or tactile alert 218 informing a user that the dose of medicinal fluid drawn into syringe 206 is more or less than the prescribed or intended dosage.

Other alterations and modifications of the invention will likewise become apparent to those of ordinary skill in the art upon reading this specification in view of the accompanying drawings, and it is intended that the scope of the invention disclosed herein be limited only by the broadest interpretation of the appended claims to which the inventors are legally entitled.

We claim:

1. A syringe dosage verification system for use prior to administering an injection of a medicinal fluid, the system comprising:

a medical syringe comprising a transparent barrel having a cylindrical fluid chamber and an outwardly facing flat indicia display surface, a plunger handle having a plunger seal slidably engaging the cylindrical fluid chamber, and a forwardly projecting hypodermic needle, wherein an entirety of a volumetric scale and associated numeric indicia are disposed on the outwardly facing flat indicia display surface between a finger flange and a nose of the barrel; and an imaging device configured to view and selectively capture a digital image of the forwardly extending end of the plunger seal as positioned inside the cylindrical fluid chamber of the barrel in relation to the entirety of the volumetric scale and the associated numeric indicia disposed on the outwardly facing flat indicia display surface between the finger flange and the nose of the barrel when a volumetric dosage of the medicinal fluid is drawn into the cylindrical fluid chamber of the barrel and when at least a portion of the outwardly facing flat indicia display surface and the entirety of the volumetric scale and the associated numeric indicia dispose on the outwardly facing flat indicia display surface between the finger flange and the nose of the barrel are disposed within a field of view of the imaging device to determine the volumetric dosage of the medicinal fluid drawn into the cylindrical fluid chamber of the barrel prior to administering the injection of the medicinal fluid.

2. The syringe dosage verification system of claim 1, wherein the imaging device is a mobile imaging device.

3. The syringe dosage verification system of claim 2, wherein the mobile imaging device is a cellular telephone.

4. The syringe dosage verification system of claim 2, wherein the mobile imaging device is a digital scanner.

5. The syringe dosage verification system of claim 2, wherein the imaging device is configured by downloading and installing application software on the imaging device.

6. The syringe dosage verification system of claim 5, wherein the application software is configured to generate an alert to notify a user if the fluid dosage drawn into the cylindrical fluid chamber of the barrel is not correct.

7. The syringe dosage verification system of claim 6, wherein the alert is at least one of an audio alert, a visual alert, and a tactile alert.

8. The syringe dosage verification system of claim 7, wherein an alert generation device is configured to generate the alert.

9. The syringe dosage verification system of claim 1, further comprising: a comparator configured to determine whether the dosage drawn into the medical syringe is within a permissible range of deviations from a predetermined value.

10. The syringe dosage verification system of claim 9, wherein the comparator is configured to notify a user of an incorrect fluid dosage drawn into the medical syringe.

11. The syringe dosage verification system of claim 1, wherein the medical syringe comprises at least one needle safety device configured to protect a user or a third party from an accidental needle stick.

12. The syringe dosage verification system of claim 11, wherein the at least one needle safety device comprises a mechanism that selectively retracts the hypodermic needle into a needle retraction chamber that is integrally molded with the cylindrical fluid chamber and the outwardly facing flat indicia display surface following use.

13. The syringe dosage verification system of claim 11, wherein the hypodermic needle has a forwardly extending needle tip, and wherein the needle safety device comprises a needle safety shield that is forwardly moveable by the user to cover the forwardly extending needle tip of the hypodermic needle following use.

14. A syringe dosage verification system for use prior to administering an injection of a medicinal fluid, the system comprising:

a medical syringe comprising:

a barrel having a nose, a finger flange, an outwardly facing flat indicia display surface disposed between the nose and the finger flange, and an inwardly facing surface defining a cylindrical fluid chamber inside the barrel, wherein an entirety of a volumetric scale is disposed on the outwardly facing flat indicia display surface between the finger flange and the nose of the barrel;

a plunger having a plunger handle and a plunger seal disposed on a distal end of the plunger handle and slidably engaging the inwardly facing surface of the cylindrical fluid chamber of the barrel; and a forwardly projecting hypodermic needle; and an imaging device configured to view and selectively capture a digital image of a position of the plunger seal relative to the entirety of the volumetric scale disposed on the outwardly facing flat indicia display surface between the finger flange and the nose of the barrel when a dosage of the medicinal fluid is drawn into the cylindrical fluid chamber of the barrel and when at least a portion of the outwardly facing flat indicia display surface and the entirety of the volumetric scale disposed on the outwardly facing flat indicia display surface between the finger flange and the nose of the barrel are within a field of view of the imaging device to determine the dosage of the medicinal fluid drawn into the cylindrical fluid chamber of the barrel prior to administering the injection.

15. The syringe dosage verification system of claim 14 further comprising a comparator configured to determine from the digital image of the position of the plunger handle relative to the barrel for a specified syringe and dosage whether a volume of medicinal fluid drawn into the medical syringe is within a permissible range of deviation from a predetermined dosage.

16. The syringe dosage verification system of claim 15, wherein the comparator is operatively coupled to an alert generation device to notify a user of an incorrect fluid dosage drawn into the medical syringe.

17. The syringe dosage verification system of claim 16, wherein the alert generation device is configured to generate at least one of an audio alert, a visual alert and a tactile alert.

18. The syringe dosage verification system of claim 14, further comprising: an alert generation device configured to notify a user of an incorrect fluid dosage drawn into the medical syringe.

19. The syringe dosage verification system of claim 14, wherein the imaging device is a mobile imaging device or digital scanner.

20. The syringe dosage verification system of claim 19, wherein the mobile imaging device is a cellular telephone.

21. The syringe dosage verification system of claim 14, wherein the imaging device is configured by downloading and installing application software on the imaging device.

22. The syringe dosage verification system of claim 21, wherein the application software is configured to generate an alert to notify a user of an incorrect fluid dosage drawn into the medical syringe.

23. The syringe dosage verification system of claim 22, wherein the alert is at least one of an audio alert, a visual alert and a tactile alert.

24. The syringe dosage verification system of claim 14, wherein the medical syringe comprises at least one needle safety device configured to protect a user or a third party from an accidental needle stick.

25. The syringe dosage verification system of claim 24, wherein the at least one needle safety device comprises a mechanism that selectively retracts the hypodermic needle into a needle retraction chamber following use.

26. The syringe dosage verification system of claim 24, wherein the hypodermic needle has a forwardly extending needle tip, and wherein the needle safety device comprises a needle safety shield that is forwardly moveable by the user to cover the forwardly extending needle tip of the hypodermic needle following use.

27. An apparatus for injecting a verified dosage of a medicinal fluid, the apparatus comprising:

a syringe comprising:

a barrel having a cylindrical fluid chamber and an outwardly facing flat indicia display surface comprising a volumetric scale, wherein a full length of the volumetric scale is disposed on the outwardly facing flat indicia display surface between a nose and a finger flange of the barrel, and wherein at least a portion of the full length of the volumetric scale overlies at least a portion of the cylindrical fluid chamber to facilitate simultaneous viewing of a medicinal fluid dosage disposed inside the cylindrical fluid chamber of the barrel and the full length of the volumetric scale disposed on the outwardly facing flat indicia display surface between the nose and the finger flange of the barrel;

a plunger handle having a plunger seal slidably engaging the cylindrical fluid chamber of the barrel; and a hypodermic needle in fluid communication with the cylindrical fluid chamber of the barrel and extending from the nose of the barrel; and an imaging device configured to view and selectively capture at least one digital image of the medicinal fluid dosage disposed inside the cylindrical fluid chamber of the barrel and the full length of the volumetric scale disposed on the outwardly facing flat indicia display surface between the nose and the finger flange of the barrel and overlying the portion of the cylindrical fluid chamber of the barrel when at least a portion of the outwardly facing flat indicia display surface and the full length of the volumetric scale disposed on the outwardly facing flat indicia display surface between the finger flange and the nose of the barrel is within a field of view of the imaging device, from which a volumetric dosage of the medicinal fluid dosage drawn into the cylindrical fluid chamber can be determined prior to injecting the medicinal fluid.

28. The apparatus of claim 27, wherein the imaging device is a mobile imaging device.

29. The apparatus of claim 28, wherein the mobile imaging device is a cellular telephone.

30. The apparatus of claim 28, wherein the mobile imaging device is a digital scanner.

31. The apparatus of claim 27, wherein the imaging device is controlled using application software installed on the imaging device.

32. The apparatus of claim 27, further comprising a comparator configured to generate an alert to notify a user of an incorrect fluid dosage drawn into the syringe.

33. The apparatus of claim 32, wherein the alert is at least one of an audio alert, a visual alert, and a tactile alert.

34. The apparatus of claim 27, wherein the syringe further comprises at least one needle safety feature configured to protect a user or a third party from an accidental needle stick.

35. The apparatus of claim 34, wherein the at least one needle safety feature comprises a mechanism that selectively retracts the hypodermic needle into a needle retraction chamber that is integrally molded with the cylindrical fluid chamber following use.

36. The apparatus of claim 34, wherein the hypodermic needle has a forwardly extending needle tip, and wherein the needle safety feature comprises a needle safety shield that is forwardly moveable by the user to cover the forwardly extending needle tip of the hypodermic needle following use.

37. The apparatus of claim 27, wherein the imaging device is configured to determine a volumetric dosage from the digital image of a plunger handle position relative to the barrel.

38. The apparatus of claim 37, wherein the imaging device determines the volumetric dosage using by a plunger position ratio calculation.

39. The apparatus of claim 37, configured for use with a syringe having a barrel that is not transparent.

40. The apparatus of claim 27, wherein the imaging device is configured to determine the volumetric dosage of the medicinal fluid dosage drawn into the cylindrical fluid chamber from the digital image of medicinal fluid dosage disposed inside the cylindrical fluid chamber of the barrel and the full length of the volumetric scale disposed on the outwardly facing flat indicia display surface between the nose and the finger flange of the barrel.

41. The apparatus of claim 27, wherein the volumetric scale is visible in relation to the plunger seal, and wherein a position of the plunger seal in relation to the volumetric scale is used to determine the volumetric dosage of the medicinal fluid dosage drawn into the cylindrical fluid chamber.

* * * * *